United States Patent [19]

Montes

[11] Patent Number: 4,985,443

[45] Date of Patent: Jan. 15, 1991

[54] METHOD AND COMPOSITION FOR TREATING VITILIGO

[76] Inventor: Leopoldo F. Montes, Buenos Aires, Argentina, 1121

[21] Appl. No.: 389,603

[22] Filed: Aug. 4, 1989

[51] Int. Cl.$^5$ .................. A61K 31/50; A61K 31/495; A61K 31/505
[52] U.S. Cl. .................................. 514/249; 514/255; 514/258
[58] Field of Search ................ 514/255, 258, 249

[56] References Cited

PUBLICATIONS

Chem. Abst., 87—165580y (1977).
Chem. Abst., 94—96876e (1981).

*Primary Examiner*—Stanley Friedman
*Attorney, Agent, or Firm*—Darby & Darby

[57] ABSTRACT

To cure vitiligo without side effects, a disease characterized by cutaneous depigmentation, a treatment consisting in the oral administration of folic acid in daily doses from 1 to 50 mg. The treatment of vitiligo with folic acid can be enhanced by also using oral vitamin C and intramuscular vitamin $B_{12}$.

6 Claims, No Drawings

METHOD AND COMPOSITION FOR TREATING VITILIGO

The present invention deals with a new treatment of patients having vitiligo by means of chemical compositions containing folic acid.

DESCRIPTION OF VITILIGO

Vitiligo is a disease which affects 1%-2% of the world population according to J. A Rook, D. S. Wilkinson and F. J. G. Ebling ( Textbook to Dermatology, Blackwell Scientific Publications, Oxford, 1979).

It results from the lack of melanin in the epidrmis due to the disappearance of melanocytes from the epidermis, as it is defined by A. S. Breathnach, S. Bohr and L. M. Wyllie in "Electron Microscopy of Peripheral Nerve Terminals and Marginal Melanocytes in Vitiligo", J. Invest. Dermat. 47:125-140, 1966.

Clinically, the patients display white areas of various sizes and shapes, either localized or generalized. Frequently, these white areas have a symmetrical distribution on both halves of the body, as described by A. B. Lerner in "Vitiligo", Am. J. Medicine, 51:141-147, 1971, and T. B. Fitzpatrick and others in "Dermatology in General Medicine", McGraw Hill, New York, 1971.

Vitiligo can begin at any age and become gradually progressive to the point of affecting the entire skin. Although the precise cause of vitiligo is not known such clinical behaviour speaks in favor on an internal or systemic etiology.

Despite extensive therapeutic efforts over the years, the treatments available are unsatisfactory, to say the least. W. B. Shelley, the great master of American Dermatology, has summarized the drama and frustration in the management of this disease, particularly in the darker skin, as follows: "the vitiliginous areas of the face are truly disfiguring. Years ago Nehru recognized this fact by ranking the need for a treatment of vitiligo on a level with that for leprosy and tuberculosis. In all instances there is a quest for help. At present the best we can offer is little. Surely in this century of moon flights, we should be able to do better . . . "W. B. Shelley, "Consultations in Dermatology", W. B. Saunders, Philadelphia, 1972).

The last edition of CURRENT THERAPY indicates that the main treatment commonly in use for vitiligo is systemic psoralen 0.5 mg/Kg ingested two hours before ultraviolet light therapy, preferably UVA (Marvin Rappaport. Conn's Current Therapy. Page 762. W. B. Saunders Co. Philadelphia, 1989)

However, psoralens together with ultraviolet light or sunlight exposure are potentially toxic and complete repigmentation is not easily achieved and obtained only after prolonged treatment in a very small percentage of patients, according to J. E Fulton and others in "Treatment of Vitiligo with Topical Methoxalen and Blacklight", Arch. Dermat. 100:224-229, 1969. Topical or intralesional steroids can be helpful in the early stages when the affected areas, as shown in biopsies, contain inflammatory cells in the upper dermis. But prolonged use does not result in permanent cure and may involve the risk of systemic absorption or local atrophy, as said by E. Kandil in "Treatment of Localized Vitiligo with Intradermal Injections of Triamcinolone Acetonide", Dermatologica, 140:195-206, 1970.

It was unexpectedly found when a patient suffering from vitiligo was given folic acid orally due to a very severe deficiency of the substance in the serum, condition known as megaloblastic anemia. The levels were so low that standard biochemical methods for the measurement of folic acid in the serum failed to detect any measurable levels. Thus the patient was placed on oral folic acid at the usual dose of 1 mg./day. After two weeks on this dose, folic acid levels became barely detectable, still far below the normal levels. So the dose was increased to 5 mg/day and maintained for a full month thus allowing to reach serum levels of 10 ng/ml. Surprisingly and unexpectedly as the anemia was being corrected, the depigmented plaques of vitiligo began to show the development of new pigment, the same color than the normal sorrounding skin. This gradual phenomenon took place in two different patterns: (a) as small round dots within the white plaques; (b) as an increased pigmentation of the borders of the plaques wich became darker and began to advance into the white zones gradually filling them in. The patient was kept on 5 mg./day of folic acid given orally after breakfast for ten months, the time which took for all the depigmented areas to regain their normal color.

DESCRIPTION OF THE INVENTION

This invention relates to the pharmaceutical composition and the method of systemic use of the same for the treatment of vitiligo. Such pharmaceutical composition is known as folic acid or pteroylglutamic acid, a preparation used before in the treatment of certain types of anemia.

Folic acid has not been previously recommended for the treatment of vitiligo. A complete search of the literature failed to reveal any instance in which folic acid was used to treat vitiligo.

The invention is a treatment of vitiligo by means of oral administration of folic acid, which is also known as pteroylglutamic acid.

Folic acid is given either in the form of capsules or tablets, ranging from one to fifty milligrams. Patients are instructed to take one to three tablets a day, the total daily dose ranging from 1 mg. to 50 mg. Folic acid is given either as a single daily dose or as divided doses of twice a day or three times a day.

The duration of the treatment is for a minimum of six months to a maximum of two years.

The favorable results obtained with this can be seen in the following table.

TABLE I

PATIENTS TREATED

| Patient | Age | Sex | Daily Dose | Duration of Treatment | Degree of Repigmentation |
|---|---|---|---|---|---|
| 1 | 55 | M | 5 mg | 6 months | 90% |
| 2 | 36 | M | 10 mg | 10 months | 80% |
| 3 | 22 | M | 5 mg | 10 months | 100% |
| 4 | 13 | M | 5 mg | 12 months | 100% |
| 5 | 65 | M | 20 mg | 12 months | 100% |
| 6 | 22 | F | 10 mg | 10 months | 90% |
| 7 | 33 | M | 30 mg | 12 months | 75% |
| 8 | 33 | F | 10 mg | 10 months | 100% |
| 9 | 59 | F | 10 mg | 10 months | 90% |
| 10 | 19 | F | 5 mg | 10 months | 75% |
| 11 | 15 | F | 5 mg | 24 months | 100% |
| 12 | 75 | F | 20 mg | 12 months | 50% |
| 13 | 48 | M | 50 mg | 9 months | 75% |
| 14 | 50 | F | 10 mg | 6 months | 60% |
| 15 | 44 | M | 50 mg | 9 months | 100% |

Folic acid is normally used in the treatment of megaloblastic anemias and is recommended in doses ranging from 0.25 to 1 mg./daily.

As a matter of fact, the largest commercially available oral dose is the 1 mg. tablet (Physicians Desk Reference, 43rd Edition, Medical Economics Co., Oradell, N.J., 1989).

Consequently, it was found the need to significantly increase this dose for the treatment of vitiligo, so new capsules and tablets had to be prepared.

Folic acid, commercially available as a yellow powder, was compounded as capsules and tablets following standard methods.

The following sizes were compounded:
CAPSULES: 1 mg/2 mg/5 mg/10 mg/20 mg/25 mg/30 mg/50 mg.
TABLETS: 1 mg/2 mg/5 mg/10 mg/20 mg/25 mg/30 mg/50 mg.

Never before have these forms and sizes of folic acid capsules and tablets been produced.

DETERMINATION OF FOLIC ACID BLOOD LEVELS IN VITILIGO PATIENTS

As according to this invention the oral administration of folic acid in vitiligo patients resulted in repigmentation, it led to study the blood levels of this substance in untreated patients with this condition.

Because of the metabolic and biochemical relationship between folic acid an vitamin $B_{12}$, the latter was also studied.

The results of this investigation is shown in TABLE II.

Fifteen patients with vitiligo were studied, as shown in TABLE II. They were otherwise clinically normal.

For quantitative determination of folic acid levels, the (125 I) Folate Radioassay Kit was employed. For quantitative determination of Vitamin $B_{12}$ levels the (57 Co) Vitamin $B_{12}$ Radioassay Kit was used. These standard methods are based on principles of competitive protein binding. Kits are commercially available from Dade, Baxter Travenol Diagnostics, Inc., 600 MemorialDrive, Cambridge, Mass. 02139.

When compared with values in the normal population, folic acid levels were diminished in a statistically significant fashion. As shown in TABLE II, out of the twelve patients, folic acid levels were below normal for ten patients in the serum ($p < 0.0001$), for five patients in the blood (p 0.10) and for six patients in the erythrocytes ($p < 0.02$). Vitamin $B_{12}$ serum levels were below normal in only three of the twelve patients.

TABLE II

| | | | Normal Values | | | |
| | | | Folic Acid | | | Vitamin |
| Patient | Age | Sex | 6–20 Serum (ng/ml) | 80–320 Blood (ng/ml) | 175–700 Erythrocytes (ng/ml) | $B_{12}$ 200–900 Serum (pg/ml) |
|---|---|---|---|---|---|---|
| 1 | 55 | M | 1.9 | 360 | 765 | 300 |
| 2 | 36 | M | 2.1 | 72 | 160 | 110 |
| 3 | 22 | M | 1.9 | 110 | 275 | 100 |
| 4 | 13 | M | 3.2 | 60 | 150 | 500 |
| 5 | 65 | M | 2.0 | 120 | 285 | 280 |
| 6 | 22 | F | 8.0 | 190 | 475 | 270 |
| 7 | 33 | M | ND* | 80 | 170 | 850 |
| 8 | 33 | F | 4.0 | 60 | 140 | 80 |
| 9 | 59 | F | 2.1 | 56 | 140 | 900 |
| 10 | 19 | F | 10.0 | 260 | 250 | 840 |
| 11 | 15 | M | 2.0 | 38 | 95 | 800 |
| 12 | 75 | F | 2.0 | 80 | 200 | 780 |

*Non Detectable

Folic acid, an indispensable factor in all tissues, contains three components: pteridine, para-aminobenzoic acid and L-glutamic acid.

Interestingly, free pteridine is the coenzyme for the enzymatic hydroxilation of phenylalanine to tyrosine, according to W. S, Beck in "Folic acid vitaminology. Hematology" 4th Edition, The MIT Press, Cambridge, Ma, 1985. Thus a deficiency in pteridine could account for a deficiency in tyrosine, the precursor of melanin. Lerner and Fitzpatrick, "Biochemistry of melanin formation", Physiological Reviews, 1950, 30:91-96, have suggested that a deficiency in tyrosine may result in deficient melanin production, the hallmark of vitiligo.

Para-aminobenzoic acid, on the other hand, may also be playing a role in pigmentation as shown by the darkening of hair following the administration of large doses of this compound, as mentioned by C. J. Zarafonetis in "Darkening of grey hair during para-aminobenzoic acid therapy", J. Invest. Dermat., 1950, 34:399–401. Frost, Dann and McIntire, "Adequacy of the known synthetic vitamins for normal feathering and pigmentation in chicks", Proc. Soc. Exper. Biol. and Med., 1946, 61:65–69, showed that folic acid alone completely restored pigment in chicks depigmented on synthetic diets. This finding was later confirmed by Lillie and Briggs, "Studies on folic acid in the prevention of abnormal feather pigmentation", Poultry Sc., 1947, 26:475-477.

According to the invention the diminished folic acid is apparently a factor in the development of vitiligo, as data demonstrates. A simultaneous evaluation of the metabolic interrelations between folic acid and vitamin C in vitiligo should be included, because as emphasized by Beck, ascorbic acid appears to increase the stability of folic acid. Dietary deficiency of vitamin C may cause an otherwise barely sufficient intake of folic acid to become insufficient. Interestingly, two of the patients in TABLE II (patients 4 and 12) showed diminished levels of vitamin C together with the low levels of folic acid.

Because of the aforementioned data on the metabolic interrelations between folic acid and vitamin C, we found that the administration of the latter in addition to folic acid it is more beneficial than giving folic acid alone in vitiligo. Consequently adding vitamin C to the early regimen of folic acid alone is recommended.

In five patients folic acid was administered in the dose of 10 mg/day given after breakfast. In these same patients, in addition, vitamin C (ascorbic acid) was given after lunch in the dose of 500 mg/day. These patients began to show depigmentation faster than patients receiving folic acid only.

In is noteworthy that in vitamin C deficiency, also known as scurvy, folic acid deficiency may occur as a secondary alteration, as W. S. Beck mentions in "Hematology", The MIT Press, Cambridge, 1985. Also vitamin C is important for the conversion of folic acid to folinic acid, according to R. W. Wilter, "Effects of Ascorbic Acid Deficiency in Man", The Vitamins, Edited by Sebrell Jr.,W. H. and Harris, R. E. Academic Press, New York, 1967.

After discovering that folic acid administration results in repigmentation of vitiligo patients, other means to increase folic acid utilization by the body were sought. For example, because some metabolic systems requiring folic acid coenzymes (such as methionine synthesis) also require vitamin $B_{12}$ derivatives, it was decided to add this vitamin to the treatment program. Thus vitamin $B_{12}$ in the dose of 1000 micrograms intramuscularly was administered to six patients once a month. These patients repigmented faster than patients receiving folic acid alone.

The effect of vitamin $B_{12}$ can be explained perhaps due to the ability of this vitamin to enhance myelin synthesis(Merck, Sharp & Dome, alpha Redisol, "Clinical Pharmacology", West Point, Penn., 1982) because the neural basis for vitiligo has been considered by many investigators since: (a) vitiligo fails to develop in areas of nerve damage; (b) vitiligo frequently adopts a segmental distribution; (c) vitiligo may develop in association with encephalitis; (d) the depigmented areas sweat more easily, as mentioned by A. B. Lerner and J. J. Nordlund in "Vitiligo. What is it?", Journal Amer.-Med.Assoc. 239:1183-1187,1978 and G. Nelhaus in "Acquired Unilateral Vitiligo and Poliosis of the Head and Subacute Encephalitis with Partial Recovery", Neurology, 20:965-974, 1970.

What I claim is:

1. A method of treating Vitiligo in a human which comprises orally administering to said human capsules or tablets containing between about 2 mg and about 50 mg of folic acid.

2. A method according to claim 1 administering at least about 2 mg of said folic acid every 24 hours.

3. The method of claims 1 or 2 which comprises continuously administering said folic acid at least once per day for between about six and about twenty four consecutive months.

4. The method of claim 1 which comprises simultaneously administering approximately 500mg per day of vitamin C and administering intramuscular injections of approximately 1000 micrograms per month of Vitamin $B_{12}$ to said human.

5. The method of claim 1 or 2 which comprises continuing said treatment for between about six and about twenty four months.

6. A method according to claim 1 administering not more than about 50mg of said folic acid every 24 hours.

* * * * *